United States Patent
Wang et al.

(10) Patent No.: US 8,710,062 B2
(45) Date of Patent: Apr. 29, 2014

(54) PIPERAZINEDIONE COMPOUNDS

(75) Inventors: Hui-po Wang, Taipei (TW); Che-Ming Teng, Taipei (TW); Chun-Li Wang, Pingzhen (TW); Jih-hwa Guh, Taipei (TW); Shiow-Lin Pan, Taipei (TW); Yuan-Yi Wang, New Taipei (TW); Jang-Feng Lian, Zhongli (TW)

(73) Assignee: Taipei Medical University, Taipei (TW)

( * ) Notice: Subject to any disclaimer, the term of this patent is extended or adjusted under 35 U.S.C. 154(b) by 0 days.

(21) Appl. No.: 13/404,534

(22) Filed: Feb. 24, 2012

(65) Prior Publication Data

US 2012/0232088 A1 Sep. 13, 2012

Related U.S. Application Data

(60) Provisional application No. 61/451,799, filed on Mar. 11, 2011.

(51) Int. Cl.
*A61K 31/496* (2006.01)
*C07D 401/14* (2006.01)

(52) U.S. Cl.
USPC ...... 514/253.01; 544/336; 544/358; 544/360; 514/252.12; 514/252.13

(58) Field of Classification Search
USPC ........ 544/336, 358, 360; 514/252.12, 252.13, 514/253.01
See application file for complete search history.

(56) References Cited

U.S. PATENT DOCUMENTS

| | | | | |
|---|---|---|---|---|
| 6,635,649 | B2 * | 10/2003 | Teng et al. | 514/253.11 |
| 7,288,545 | B2 | 10/2007 | Teng et al. | |
| 7,919,497 | B2 * | 4/2011 | Palladino et al. | 514/255.06 |
| 7,935,704 | B2 * | 5/2011 | Palladino et al. | 514/252.19 |
| 8,129,527 | B2 * | 3/2012 | Palladino et al. | 544/337 |
| 2011/0065691 | A1 | 3/2011 | Kaplan et al. | |

FOREIGN PATENT DOCUMENTS

| | | |
|---|---|---|
| WO | WO96/20179 | 7/1996 |
| WO | WO2011/084962 | 7/2011 |
| WO | WO2012/035436 | 3/2012 |

OTHER PUBLICATIONS

Wang et al (2002): STN International HCAPLUS database, (Columbus, Ohio), Accession No. 2002:585058.*
Yamazaki et al.; "Synthesis and structure-activity relationship study of antimicrotubule agents phenylahistin derivatives with a didehydropiperazine-2,5-dion structure"; Journal of Medicinal Chemistry 55(3):1056-1071 (2012).
Yamazaki et al.; "Tubulin Photoaffinity labeling study with a plinabulin chemical probe possessing a biotin tag at the oxazole" Bioorganic & Medicinal Chemistry; 19(1):595-602 (2011).
Yokoya et al.; "Chemistry of renieramycins. Part 9: Stereocontrolled total synthesis of (±)-renieramycin G"; Tetrahedron Letters; 52(19):2446-2449 (2011).
Ando et al.; "Diastereoselective synthesis of diketopiperazine bis-α,β-epoxides"; Journal of Organic Chemistry; 76(4):1155-1158 (2011).

* cited by examiner

*Primary Examiner* — Golam M M Shameem
(74) *Attorney, Agent, or Firm* — Cesari and McKenna, LLP

(57) ABSTRACT

This invention relates to piperazinedione compounds shown in the specification. These compounds are tyrosine kinase inhibitors and can be used to treat cancer.

11 Claims, No Drawings

PIPERAZINEDIONE COMPOUNDS

CROSS-REFERENCE TO RELATED APPLICATIONS

This application claims the priority of U.S. Provisional Application No. 61/451,799, filed on Mar. 11, 2011. The contents of the application are hereby incorporated by reference in its entirety.

BACKGROUND

Tyrosine kinase is an enzyme that transfers a phosphate group from ATP to a protein, resulting in attachment of the phosphate group to a tyrosine in the protein.

Phosphorylation of a tyrosine in a protein provides a mechanism via which cellular oncogenes deregulate various signaling pathways and thereby induce transformation. Tyrosine kinase is therefore an important target for anticancer therapy. See Van der Geer, P., Hunter, T. and Lindberg, R. A. *Annu. Rev. Cell Biol.*, 1994, 10, 251; Levitzki, A. and Gazit, A. *Science*, 1995, 267, 1782; and Marshall, C. J. *Cell*, 1995, 80, 179.

SUMMARY

This invention is based on the unexpected discovery that a group of piperazinedione compounds effectively inhibit tyrosine kinase and suppress cancer growth.

In one aspect, this invention relates to a piperazinedione compound having formula (I):

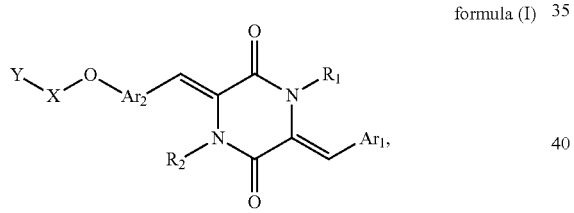

formula (I)

in which each of $R_1$ and $R_2$, independently, is H, $C_{1-5}$ alkyl, or $C(O)$—$C_{1-5}$ alkyl; each of $Ar_1$ and $Ar_2$, independently, is aryl or heteroaryl; X is $C_{1-3}$ alkylene, C(O), or C(O)—$C_{1-3}$ alkylene; and Y is heterocycloalkyl or heteroaryl.

Referring to formula (I), the above-described piperazinedione compounds may feature that X is $CH_2$, $Ar_1$ is phenyl, $Ar_2$ is pyridinyl (e.g., pyridin-2-yl, pyridin-3-yl, or pyridin-4-yl), or Y is pyridinyl (e.g., pyridin-2-yl, pyridin-3-yl, or pyridin-4-yl).

In another aspect, this invention relates to a piperazinedione compound having formula (II):

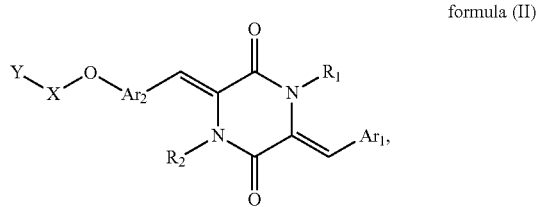

formula (II)

in which each of $R_1$ and $R_2$, independently, is H, $C_{1-5}$ alkyl, or $C(O)$—$C_{1-5}$ alkyl; each of $Ar_1$ and $Ar_2$, independently, is aryl or heteroaryl; X is $C_{1-3}$ alkylene substituted with amino or alkylcarbonylamino, C(O), or C(O)—$C_{1-3}$ alkylene substituted with amino or alkylcarbonylamino; and Y is $C_{1-5}$ alkyl, cycloalkyl, heterocycloalkyl, aryl, or heteroaryl.

Referring to formula (II), the above-described piperazinedione compounds may feature that $Ar_1$ is phenyl; $Ar_2$ is pyridinyl; X is alkylene substituted with amino or alkylcarbonylamino or X is C(O) or C(O)—$C_{1-3}$ alkylene substituted with amino or alkylcarbonylamino, or Y is phenyl.

In still another aspect, this invention relates to a piperazinedione compound having formula (III):

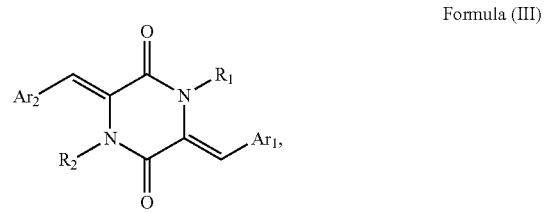

Formula (III)

in which each of $R_1$ and $R_2$, independently, is H or $C_{1-5}$ alkyl; $Ar_1$ is aryl or heteroaryl; and $Ar_2$ is quinolinyl.

Referring to formula (III), the above-described piperazinedione compounds may feature that $Ar_1$ is phenyl, pyridinyl, thiophenyl, or quinolinyl or $Ar_2$ is quinolin-2-yl or 4-quinolin-4-yl.

The term "alkyl" refers to a saturated, linear or branched, non-aromatic hydrocarbon moiety, such as $CH_3$, —$CH_2$—, or branched $C_3H_7$. The term "heterocycloalkyl" refers to a saturated non-aromatic cyclic moiety having at least one ring heteroatom, such as 4-tetrahydropyranyl. The term "aryl" refers to a hydrocarbon moiety having one or more aromatic rings. Examples of an aryl moiety include phenyl, phenylene, naphthyl, naphthylene, pyrenyl, anthryl, and phenanthryl. The term "heteroaryl" refers to a moiety having one or more aromatic rings that contain at least one heteroatom. Examples of a heteroaryl moiety include furyl, furylene, fluorenyl, pyrrolyl, thienyl, oxazolyl, imidazolyl, thiazolyl, pyridyl, pyrimidinyl, quinazolinyl, quinolyl, isoquinolyl and indolyl.

Alkyl, heterocycloalkyl, aryl, and heteroaryl mentioned herein include both substituted and unsubstituted moieties. Examples of substituents for cycloalkyl, heterocycloalkyl, aryl, and heteroaryl include $C_1$-$C_{10}$ alkyl, $C_2$-$C_{10}$ alkenyl, $C_2$-$C_{10}$ alkynyl, $C_3$-$C_8$ cycloalkyl, $C_5$-$C_8$ cycloalkenyl, $C_1$-$C_{10}$ alkoxy, aryl, aryloxy, heteroaryl, heteroaryloxy, amino, $C_1$-$C_{10}$ alkylamino, $C_1$-$C_{20}$ dialkylamino, arylamino, diarylamino, hydroxyamino, alkoxyamino, alkylsulfonamide, arylsulfonamide, hydroxy, halogen, thio, $C_1$-$C_{10}$ alkylthio, arylthio, cyano, nitro, mercapto, carbamido, carbamoyl, thioureido, thiocyanato, sulfonamido, acyl, acyloxy, carboxyl, and carboxylic ester. Examples of substituents for alkyl include all of the above substitutents except $C_1$-$C_{10}$ alkyl, $C_2$-$C_{10}$ alkenyl, and $C_2$-$C_{10}$ alkynyl. Heterocycloalkyl can also be fused with aryl or heteroaryl.

Shown in the table below are exemplary compounds of this invention.
| Compound series | Structure | |
|---|---|---|
| 1 | 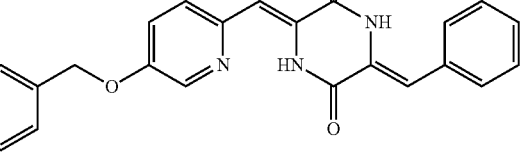 | |
| 2 | 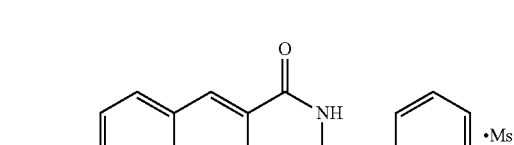 | •MsOH |
| 3 | 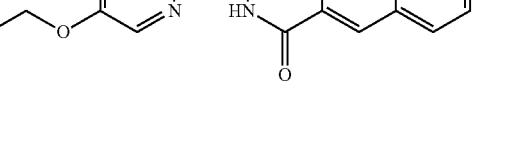 | •MsOH |
| 4 | 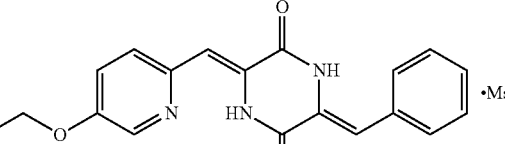 | •MsOH |
| 5 | 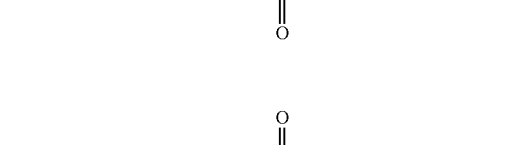 | |
| 6 | 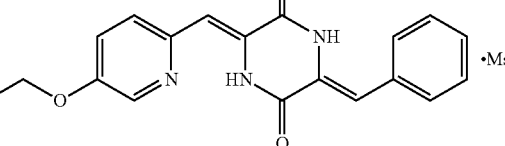 | |

-continued
| Compound series | Structure |
|---|---|
| 7 | 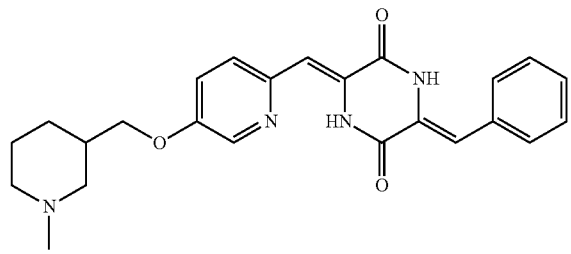 [SMILES: CN1CCCC(COc2ccc(/C=c3\[nH]c(=O)/c(=C/c4ccccc4)[nH]c3=O)nc2)C1] |
| 8 | 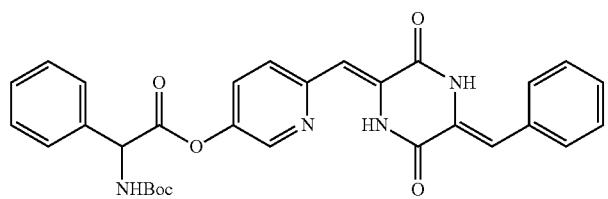 [SMILES: CC(C)(C)OC(=O)NC(C(=O)Oc1ccc(/C=c2\[nH]c(=O)/c(=C/c3ccccc3)[nH]c2=O)nc1)c1ccccc1] |
| 9 | 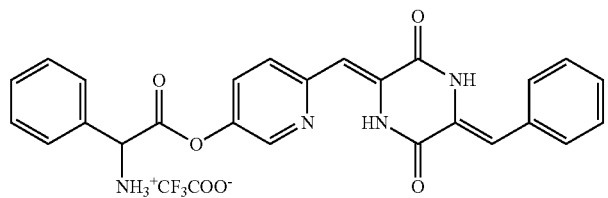 |
| 10 | 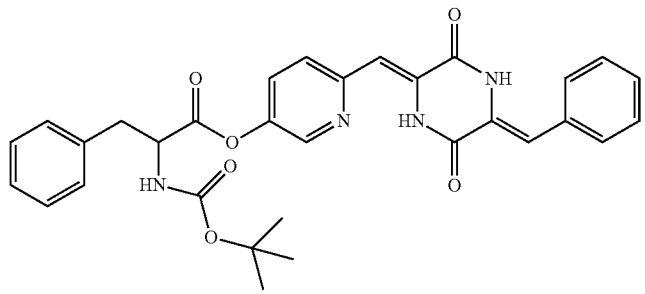 [SMILES: CC(C)(C)OC(=O)NC(Cc1ccccc1)C(=O)Oc1ccc(/C=c2\[nH]c(=O)/c(=C/c3ccccc3)[nH]c2=O)nc1] |
| 11 | 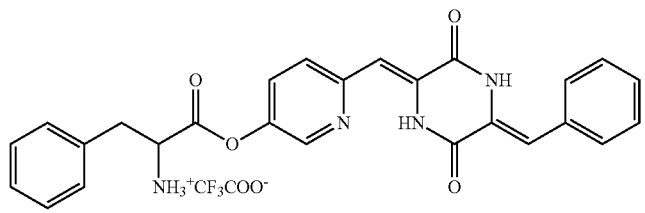 |
| 12 | 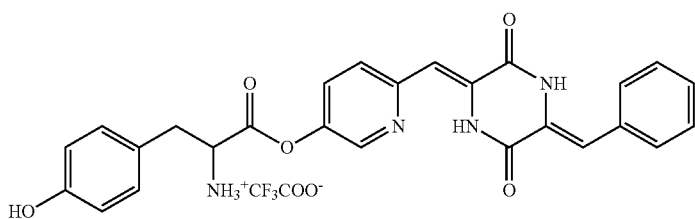 |

-continued

| Compound series | Structure |
|---|---|
| 13 | 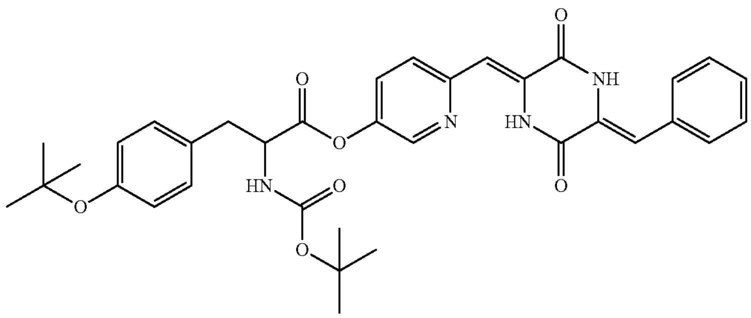 [SMILES: CC(C)(C)OC(=O)NC(Cc1ccc(OC(C)(C)C)cc1)C(=O)Oc1ccc(/C=c2\[nH]c(=O)/c(=C/c3ccccc3)[nH]c2=O)nc1] |
| 14 | 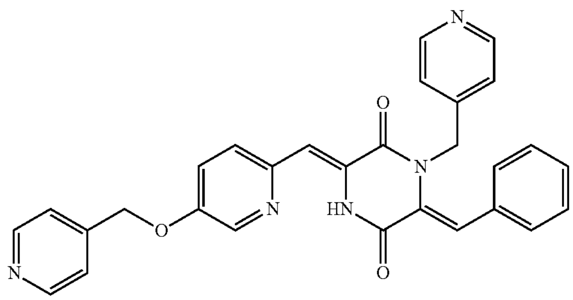 [SMILES: O=c1[nH]/c(=C\c2ccc(OCc3ccncc3)cn2)c(=O)n(Cc2ccncc2)/c1=C\c1ccccc1] |
| 15 | 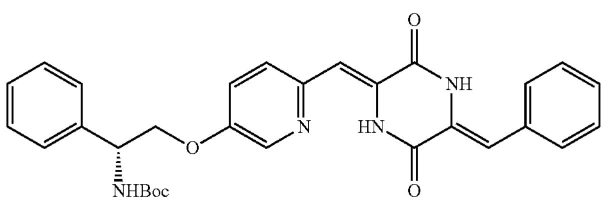 [SMILES: CC(C)(C)OC(=O)N[C@@H](COc1ccc(/C=c2\[nH]c(=O)/c(=C/c3ccccc3)[nH]c2=O)nc1)c1ccccc1] |
| 16 | 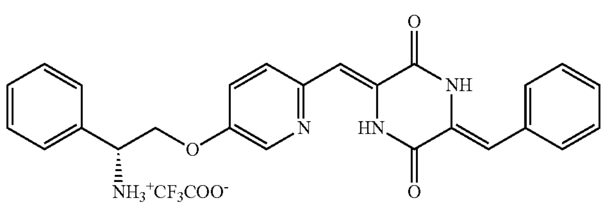 |
| 17 | 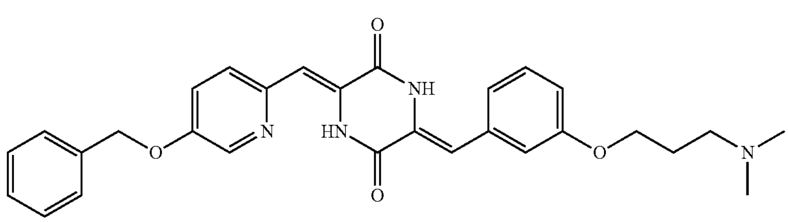 [SMILES: CN(C)CCCOc1cccc(/C=c2\[nH]c(=O)/c(=C/c3ccc(OCc4ccccc4)cn3)[nH]c2=O)c1] |
| 18 | 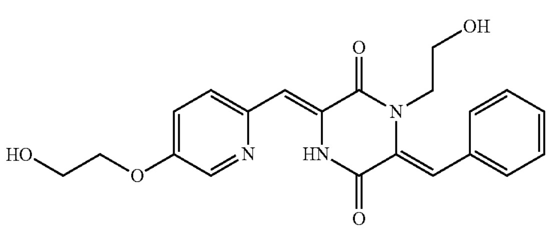 [SMILES: O=c1[nH]/c(=C\c2ccc(OCCO)cn2)c(=O)n(CCO)/c1=C\c1ccccc1] |

| Compound series | Structure |
|---|---|
| 19 | 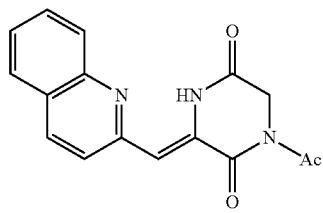 [SMILES: CC(=O)N1CC(=O)N/C(=C\c2ccc3ccccc3n2)C1=O] |
| 20 | 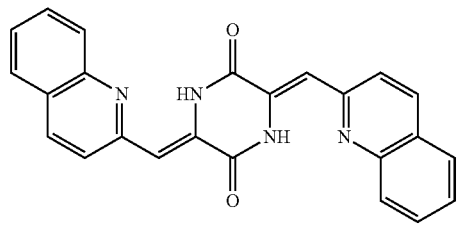 [SMILES: O=c1[nH]/c(=C\c2ccc3ccccc3n2)c(=O)[nH]/c1=C\c1ccc2ccccc2n1] |
| 21 | 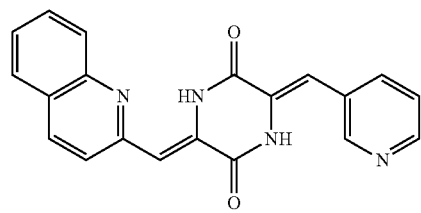 [SMILES: O=c1[nH]/c(=C\c2ccc3ccccc3n2)c(=O)[nH]/c1=C\c1cccnc1] |
| 22 | 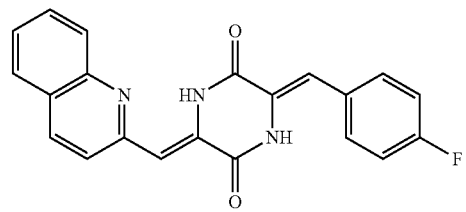 [SMILES: O=c1[nH]/c(=C\c2ccc3ccccc3n2)c(=O)[nH]/c1=C\c1ccc(F)cc1] |
| 23 | 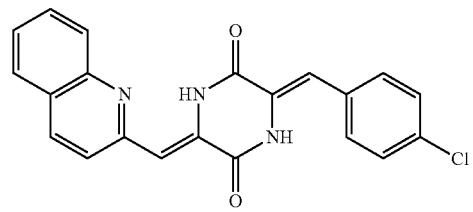 [SMILES: O=c1[nH]/c(=C\c2ccc3ccccc3n2)c(=O)[nH]/c1=C\c1ccc(Cl)cc1] |
| 24 | 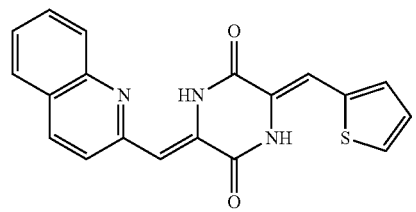 |
| 25 | 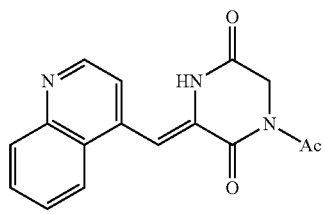 [SMILES: CC(=O)N1CC(=O)N/C(=C\c2ccnc3ccccc23)C1=O] |

| Compound series | Structure |
| --- | --- |
| 26 | 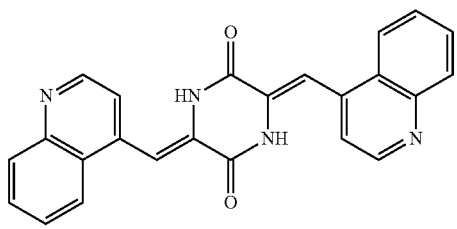 [SMILES: O=c1[nH]/c(=C\c2ccnc3ccccc23)c(=O)[nH]/c1=C\c1ccnc2ccccc12] |
| 27 | 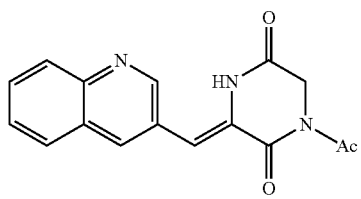 [SMILES: CC(=O)N1CC(=O)N/C(=C\c2cnc3ccccc3c2)C1=O] |
| 28 | 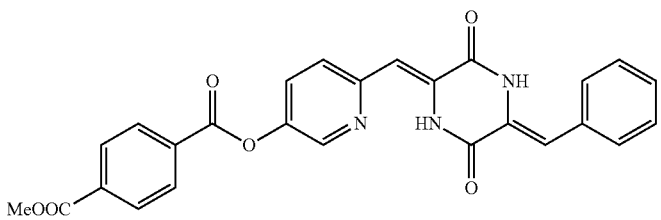 [SMILES: COC(=O)c1ccc(C(=O)Oc2ccc(/C=c3\[nH]c(=O)/c(=C/c4ccccc4)[nH]c3=O)nc2)cc1] |
| 29 | 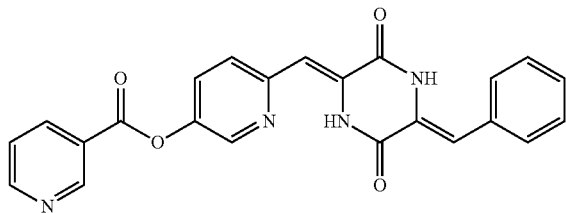 [SMILES: O=C(Oc1ccc(/C=c2\[nH]c(=O)/c(=C/c3ccccc3)[nH]c2=O)nc1)c1cccnc1] |
| 30 | 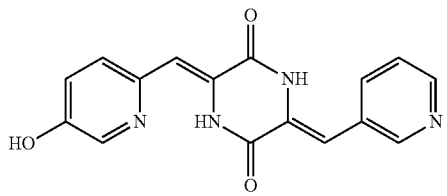 [SMILES: O=c1[nH]/c(=C\c2ccc(O)cn2)c(=O)[nH]/c1=C\c1cccnc1] |

The piperazinedione compounds described above include the compounds themselves, as well as their salts and their prodrugs, if applicable. A salt, for example, can be formed between an anion and a positively charged group (e.g., amino) on a piperazinedione compound. Suitable anions include chloride, bromide, iodide, sulfate, nitrate, phosphate, citrate, methanesulfonate, trifluoroacetate, acetate, tosylate, and napsylate. Likewise, a salt can also be formed between a cation and a negatively charged group (e.g., carboxylate) on a piperazinedione compound. Suitable cations include sodium ion, potassium ion, magnesium ion, calcium ion, and an ammonium cation such as tetramethylammonium ion. Examples of prodrugs include esters and other pharmaceutically acceptable derivatives, which, upon administration to a subject, are capable of providing active piperazinedione compounds.

In further another aspect, this invention relates to a method for treating cancer. The method includes administering to a subject in need thereof an effective amount of a piperazinedione compound having formula (I), (II), or (III).

Also within the scope of this invention is a composition containing one or more of the piperazinedione compounds described above for use in treating cancer, and the use of such a composition for the manufacture of a medicament for the just-mentioned treatment.

The details of one or more embodiments of the invention are set forth in the description below. Other features, objects, and advantages of the invention will be apparent from the description and from the claims.

DETAILED DESCRIPTION

The piperazinedione compounds described above can be prepared by methods well known in the art. The scheme shown below depicts a synthetic route to piperazinedione compounds of this invention. One can react a piperazine-2,5- dione compound with an aryl- or heteroaryl-formaldehyde to produce an intermediate aryl/heteroaryl-methylidene-piperazine-2,5-dione. The intermediate can then be treated with a ketone or another formaldehyde, followed by a base treatment, to produce a mixture of piperazinedione isomers, which are in cis- or trans- or E- or Z-double bond isomeric forms. The desired isomeric product can be separated by high pressure liquid chromatography (HPLC).

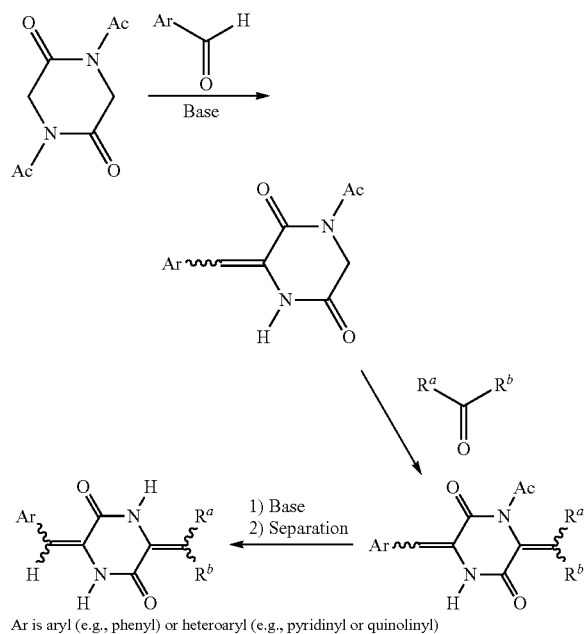

Ar is aryl (e.g., phenyl) or heteroaryl (e.g., pyridinyl or quinolinyl)

The aryl- or heteroaryl-aldehyde used above can be substituted with various functional groups, such as alkoxy. As a result, the aryl or heteroaryl ring in the piperazinedione compounds can also be substituted. Functional groups can also be introduced into the aryl/heteroaryl ring by subsequent modifications.

The chemicals used in the above-described synthetic route may include, for example, solvents, reagents, catalysts, protecting group and deprotecting group reagent. In addition, various synthetic steps may be performed in an alternate sequence or order to give the desired piperazinedione compounds. Synthetic chemistical transformations and protecting group methodologies (protection and deprotection) useful in synthesizing applicable piperazinedione compounds are known in the art and include, for example, those described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

A piperazinedione compound thus synthesized can be further purified by a method such as column chromatography, high-pressure liquid chromatography, or recrystallization.

Note that the piperazinedione compounds contain at least two double bonds, and may further contain one or more asymmetric centers. Thus, they can occur as racemates and racemic mixtures, single enantiomers, individual diastereomers, diastereomeric mixtures, and cis- or trans- or E- or Z-double bond isomeric forms. All such isomeric forms are contemplated.

Also within the scope of this invention is a pharmaceutical composition contains an effective amount of at least one piperazinedione compound described above and a pharmaceutical acceptable carrier. Further, this invention covers a method of administering an effective amount of one or more of piperazinedione compounds to a subject with cancer. Such a subject can be identified by a health care professional based on results from any suitable diagnostic method.

As used herein, the term "treating" refers to administering an active compound to a subject that has cancer, or has a symptom of or a predisposition toward it, with the purpose to cure, heal, alleviate, relieve, alter, remedy, ameliorate, improve, affect, or reduce the risk of cancer, the symptoms of or the predisposition toward cancer. The term "an effective amount" refers to the amount of the active agent that is required to confer the intended therapeutic effect in the subject. One can determine it by first testing various amounts on an animal model (e.g., mice). The interrelationship of the effective amounts for animals and humans (based on milligrams per meter squared of body surface) is described in Freireich et al., (1966) *Cancer Chemother Rep* 50: 219. Effective amounts may vary, as recognized by those skilled in the art, depending on route of administration, excipient usage, and the possibility of co-usage with other agents. They can range from about 0.1 mg/Kg to about 100 mg/Kg.

Cancer includes both solid and haematological tumours of various organs. Examples of solid tumors include pancreatic cancer; bladder cancer; colon cancer; breast cancer, including metastatic breast cancer; prostate cancer, including androgen-dependent and androgen-independent prostate cancer; renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; melanoma; esophageal cancer; head and neck cancer, including, e.g., squamous cell carcinoma of the head and neck; melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; central nervous system cancer, bone cancer; and soft tissue sarcoma. Examples of hematologic malignancy include acute myeloid leukemia (AML); chronic myelogenous leukemia (CML), including accelerated CML and CML blast phase (CML-BP); acute lymphoblastic leukemia (ALL); chronic lymphocytic leukemia (CLL); Hodgkin's disease (HD); non-Hodgkin's lymphoma (NHL), including follicular lymphoma and mantle cell lymphoma; B-cell lymphoma; T-cell lymphoma; multiple myeloma (MM); Waldenstrom's macroglobulinemia; myelodysplastic syndromes (MDS), including refractory anemia (RA), refractory anemia with ringed siderblasts (RARS), (refractory anemia with excess blasts (RAEB), and RAEB in transformation (RAEB-T); and myeloproliferative syndromes.

To practice the method of the present invention, a composition having one or more of the above-mentioned compounds can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, intraperitoneal, intratracheal or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions, and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art. A composition having one or more active above-described compounds can also be administered in the form of suppositories for rectal administration.

A pharmaceutically acceptable carrier is routinely used with one or more active above-mentioned compounds. The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an above-mentioned compound. Examples of other carriers include colloidal silicon oxide, magnesium stearate, cellulose, sodium lauryl sulfate, and D&C Yellow #10.

The piperazinedione compounds of this invention can be preliminarily screened for their efficacy in treating cancer by an in vitro assay (See Examples 15-17 below) and then confirmed by in vivo assay. Other methods will also be apparent to those of ordinary skill in the art.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

Example 1

Synthesis of 3-benzylidene-6-((5-(pyridin-4-ylmethoxy)pyridin-2-yl)methylene)piperazine-2,5-dione (Compound 1)

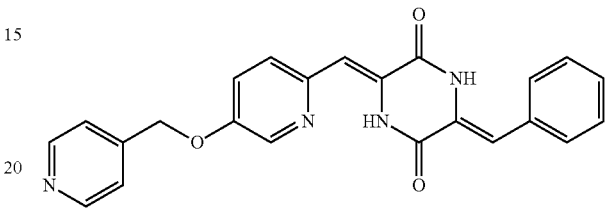

1,4-Diacetyl-piperazine-2,5-dione (8.6 g) was added to a solution of 5-benzyoxypyridin-2-yl-formaldehyde (4.0 g) in 5.6 mL of triethylamine and 40 mL of dimethylformamide. The mixture was stirred at room temperature for 16 hr and then cooled at an ice bath to produce a yellow precipitate. The precipitate was then collected and washed with ethyl acetate to give 5.4 g (77%) of 1-acetyl-3-[(5-benzyloxypyridin-2-yl) methylidene]piperazine-2,5-dione (Compound A). mp: 189-191° C.; $^1$H-NMR (400 MHz, DMSO): δ 2.52 (s, 3H), 4.54 (s, 3H), 4.33 (s, 2H), 5.52 (s, 2H), 6.85 (s, 1H), 7.384-7.488 (m, 5H, aromatic), 7.499 (d, J=8.8, 1H), 7.689 (d, J=8.8, 1H), 8.533 (s, 1H), and 12.147 (s, 1H).

Compound A (3.51 g) was added to a 40 mL of dimethylformamide solution containing benzaldehyde (1 eq.) and 4 equivalents of triethylamine (4 eq.). The solution was refluxed at 60° C. for 16 hr and cooled at an ice bath to produce a yellow precipitate. The precipitate was then collected and washed with ethyl acetate to give 3.3 g (83%) of 3-[(5-benzyloxypyridin-2-yl)methylidene]-6-(benzylmethylidene)piperazine-2,5-dione (Compound B). mp: 223-225° C.; $^1$H-NMR (400 MHz, DMSO): δ 5.243 (s, 2H), 6.695 (s, 1H), 6.812 (s, 1H), 7.346-7.634 (m, 12H, aromatic), 8.528 (s, 1H), 10.245 (s, 1H), and 12.289 (s, 1H).

Compound B (0.5 g) and NaOH (0.5 g) were dissolved in 100 mL of methanol. The mixture was hydrogenated in the presence of 0.5 g of palladium/charcoal under 1 atmospheric pressure. After the completion of the reaction as monitored by TLC, the catalyst was removed by filtration and the filtrate was evaporated in vacuo to produce a residue, which was dissolved with 50 mL of water. The obtained aqueous solution was adjusted to PH=7. A precipitate was formed and collected to give a 0.27 g (70%) of 3-[(5-hydroxypyrid-in-2-yl)methylidene]-6-(benzylmethylidene)piperazine-2,5-dione (Compound C). $^1$H-NMR (400 MHz, CDCl$_3$): δ 6.758 (s, 1H), 7.087 (s, 1H), 7.290-7.580 (m, 7H, aromatic), 8.328 (s, 1H), and 12.289 (s, 1H).

A mixture of Compound C (1 g), 4-(bromomethyl)pyridine (2 g), sodium carbonate (2 g), and DMF (50 mL) were stirred at 100° C. for 16 hr and cooled at an ice bath to produce a yellow precipitate. The precipitate was then collected and washed with water to give 0.38 g (30%) of 3-benzylidene-6-((5-(pyridin-4-ylmethoxy)pyridin-2-yl)methylene)piperazine-2,5-dione (Compound 1). mp 254-255° C.; $^1$H-NMR (400 MHz, CDCl$_3$), δ 5.26 (s, 2H) 6.78 (s, 1H), 7.11 (s, 1H), 7.31-7.59 (m, 9H), 8.20 (s, 1H), 8.48 (dd, J=2.8 Hz, 1H),), 8.72, (s, 2H), 12.50 (s, 1H).

Example 2

Synthesis of 3-benzylidene-6-((5-(pyridin-4-yl-methoxy)pyridin-2-yl)methylene)piperazine-2,5-dione methanesulfonic acid salt (Compound 2)

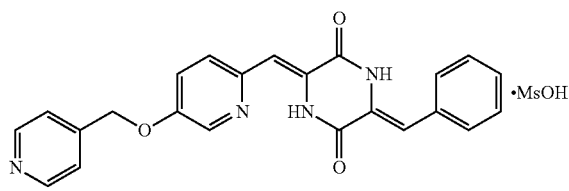 [SMILES: "·MsOH" ; O=c1[nH]/c(=C\c2ccc(OCc3ccncc3)cn2)c(=O)[nH]/c1=C\c1ccccc1]

Compound 1 was co-precipitated with equal mole of methane sulfonic acid in DMF to get yellow powder as salt product Compound 2. mp 278° C.; $^1$H-NMR (400 MHz, DMSO): δ 2.31 (s, 3H), 5.52 (s, 2H), 6.73 (s, 1H), 6.80 (s, 1H), 7.30-8.80 (m, 12H), 10.28 (s, 1H), 12.29 (s, 1H).

Example 3

Synthesis of 3-benzylidene-6-((5-(pyridin-3-yl-methoxy)pyridin-2-yl)methylene)piperazine-2,5-dione methanesulfonic acid salt (Compound 3)

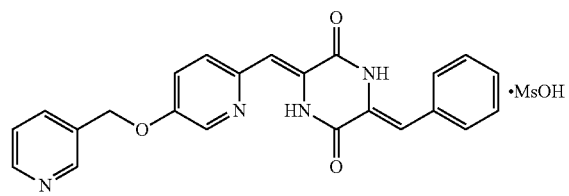 [SMILES: "·MsOH" ; O=c1[nH]/c(=C\c2ccc(OCc3cccnc3)cn2)c(=O)[nH]/c1=C\c1ccccc1]

Compound 3 was prepared in a manner similar to that described in Example 2. mp 228-230° C.; $^1$H-NMR (400 MHz, DMSO): δ 2.32 (s, 3H), 5.38 (s, 2H), 6.73 (s, 1H), 6.84 (s, 1H), 7.29-8.66 (m, 12H), 10.29 (s, 1H), 12.31 (s, 1H).

Example 4

Synthesis of 3-benzylidene-6-((5-(pyridin-2-yl-methoxy)pyridin-2-yl)methylene)piperazine-2,5-dione methanesulfonic acid salt (Compound 4)

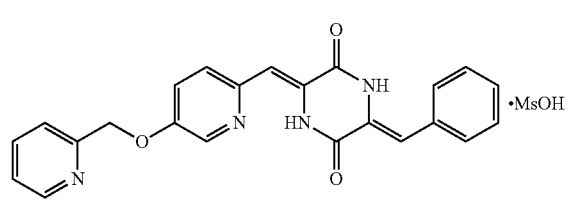 [SMILES: "·MsOH" ; O=c1[nH]/c(=C\c2ccc(OCc3ccccn3)cn2)c(=O)[nH]/c1=C\c1ccccc1]

Compound 4 was prepared in a manner similar to that described in Example 2. mp 266-267° C.; $^1$H-NMR (400 MHz, DMSO): δ 2.51 (s, 3H), 5.38 (s, 2H), 6.74 (s, 1H), 6.84 (s, 1H), 7.33-8.83 (m, 12H), 10.27 (s, 1H), 12.30 (s, 1H).

Example 5

Synthesis of 6-((Z)—((Z)-5-benzylidene-3,6-dioxopiperazin-2-ylidene) methyl)pyridin-3-yl isonicotinate (Compound 5)

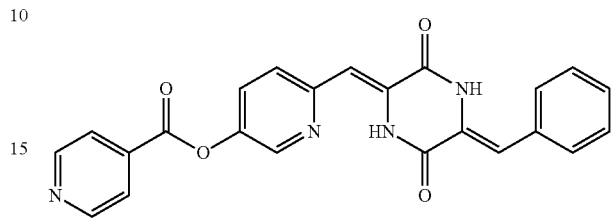

Compound 5 was prepared in a manner similar to that described in Example 1. mp 262~264° C.; $^1$H-NMR (400 MHz, CDCl$_3$): δ 6.84 (s, 1H), 7.13 (s, 1HH), 7.54-7.39 (m, 6H), 7.72 (dd, J=2.8, 8.4 Hz, 1H), 8.04 (d, J=5.6 Hz, 2H), 8.29 (s, 1H), 8.65 (d, J=2.4 Hz, 1H), 8.93 (d, J=5.6 Hz, 2H), 12.48 (s, 1H).

Example 6

Synthesis of 6-((Z)—((Z)-5-benzylidene-3,6-dioxopiperazin-2-ylidene)methyl)pyridin-3-yl-4-methylpiperazine-1-carboxylate (Compound 6)

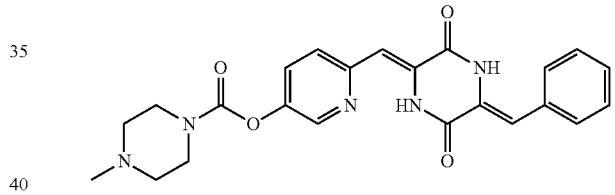

Compound 6 was prepared in a manner similar to that described in Example 1. mp 234-235° C.; $^1$H-NMR (400 MHz, CDCl$_3$): δ 2.49 (s, 3H), 2.66 (s, 4H), 3.80 (s, 4H), 6.80 (s, 1H), 7.12 (s, 1H), 7.38-7.61 (m, 7H), 8.23, (s, 1H) 8.51 (d, J=2.8 Hz, 1H), 12.54 (s, 1H).

Example 7

Synthesis of (3Z,6Z)-3-benzylidene-6-((5-((1-methylpiperidin-3-yl)methoxy)pyridin-2-yl)methylene) piperazine-2,5-dione (Compound 7)

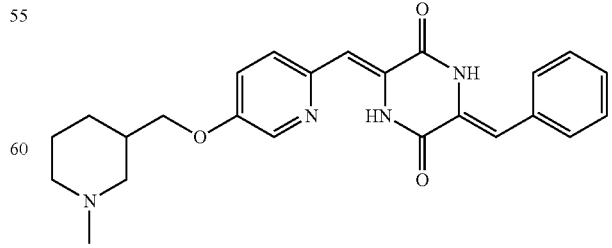

Compound 7 was prepared in a manner similar to that described in Example 1. mp: 326~328° C.; $^1$H NMR (400

MHz, DMSO): δ 8.50 (s, 1H), 7.3~7.7 (m, 7H), 6.83 (s, 1H), 6.74 (s, 1H), 4.01 (m, 2H), 2.6~2.85 (m, 2H), 1.0~2.1 (m, 7H), 2.16 (s, 3H).

Example 8

Synthesis of 6-((Z)—((Z)-5-benzylidene-3,6-dioxopiperazin-2-ylidene) methyl)pyridin-3-yl 2-(tert-butoxycarbonylamino)-2-phenylacetate (Compound 8)

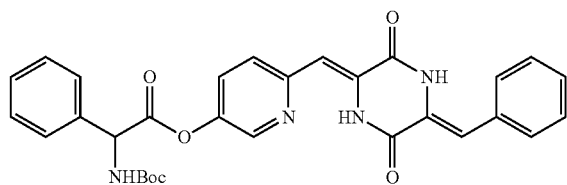 [SMILES: CC(C)(C)OC(=O)NC(C(=O)Oc1ccc(/C=c2\[nH]c(=O)/c(=C/c3ccccc3)[nH]c2=O)nc1)c1ccccc1]

2-(Tert-butoxycarbonylamino)-2-phenylacetic acid was dissolved in DMF and treated with HBTU. Compound C were then added into the mixture and stirred. After the completion of reaction, the reaction mixture was partitioned by $K_2CO_{3(aq)}$ and $CH_2Cl_2$. The organic layer was collected, dried over $MgSO_{4(s)}$, and dried by rotary evaporator. The solid residues were then purified by column chromatography to get Compound 8. mp 198° C.; $^1$H-NMR (400 MHz, CDCl$_3$): δ 1.50 (s, 9H), 5.48 (s, 1H), 5.58-5.59 (m, 1H), 6.78 (s, 1H), 7.11 (s, 1H), 7.37-7.50 (m, 13H), 8.22 (s, 1H), 8.42 (s, 1H), 12.46 (s, 1H).

Example 9

Synthesis of 2-(6-((Z)—((Z)-5-benzylidene-3,6-dioxopiperazin-2-ylidene) methyl)py-ridin-3-yloxy)-2-oxo-1-phenylethanaminium 2,2,2-trifluoroacetate (Compound 9)

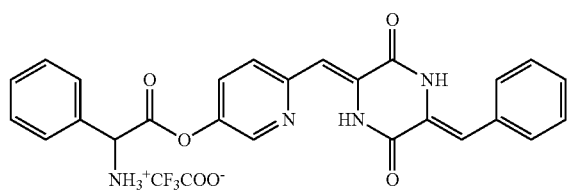

Compound 8 (0.126 g) was dissolved in 10 mL of dichloromethane and then 2.5 mL of trifluoroacetic acid was added slowly at 0° C. The reaction mixture was stirred at 0° C. and monitored by TLC until the starting material disappeared. It was concentrated by rotary evaporator to a give a crude compound, which was recrystallized in acetonitrile to give Compound 9 as a yellow solid (71%). mp 280° C.; $^1$H-NMR (400 MHz, DMSO): δ 5.69 (s, 1H), 6.79 (s, 1H), 6.86 (s, 1H), 7.34-7.38 (m, 1H), 7.44 (dd, J=7.6 Hz, 7.6 Hz, 2H), 7.55-7.58 (m, 5H), 7.65-7.67 (m, 2H), 7.71-7.74 (m, 1H), 7.80-7.82 (m, 1H), 8.59 (s, 1H), 8.91 (br, 3H), 10.42 (br, 1H), 12.16 (s, 1H).

Example 10

Synthesis of 6-((Z)—((Z)-5-benzylidene-3,6-dioxopiperazin-2-ylidene)methyl)pyridin-3-yl 2-(tert-butoxycarbonylamino)-3-phenylpropanoate (Compound 10)

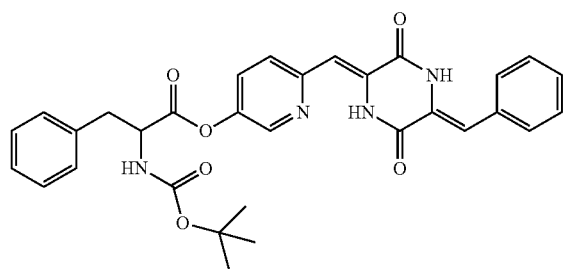 [SMILES: CC(C)(C)OC(=O)NC(Cc1ccccc1)C(=O)Oc1ccc(/C=c2\[nH]c(=O)/c(=C/c3ccccc3)[nH]c2=O)nc1]

Compound 10 was prepared in a manner similar to that described in Example 8. mp 188° C.; $^1$H-NMR (500 MHz, CDCl$_3$), δ 1.53 (s, 9H), 3.23 (m, 2H), 4.83 (m, 1H,), 5.06 (d, J=7.2 Hz, 1H) 6.76 (s, 1H), 7.10 (s, 1H), 7.29-7.62 (m, 12H), 8.22 (s, 1H), 8.36 (s, 1H), 12.44 (s, 1H).

Example 11

Synthesis of 1-(6-((Z)—((Z)-5-benzylidene-3,6-dioxopiperazin-2-ylidene)methyl)-pyridin-3-yloxy)-1-oxo-3-phenylpropan-2-aminium 2,2,2-trifluoroacetate (Compound 11)

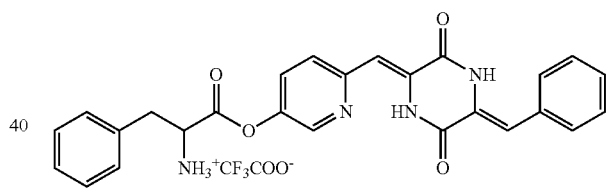

Compound 11 was prepared in a manner similar to that described in Example 9. mp 285-286° C.; $^1$H-NMR (500 MHz, CDCl$_3$), δ 3.23 (m, 2H), 4.83 (m, 1H), 5.06 (d, J=7.2 Hz, 1H), 5.28 (m, 2H), 6.76 (s, 1H), 7.10 (s, 1H), 7.29-7.62 (m, 12H), 8.22 (s, 1H), 8.36 (s, 1H), 12.44 (s, 1H).

Example 12

Synthesis of 1-(6-((Z)—((Z)-5-benzylidene-3,6-dioxopiperazin-2-ylidene)methyl)pyridin-3-yloxy)-3-(4-hydroxyphenyl)-1-oxopropan-2-aminium 2,2,2-trifluoroacetate (Compound 12)

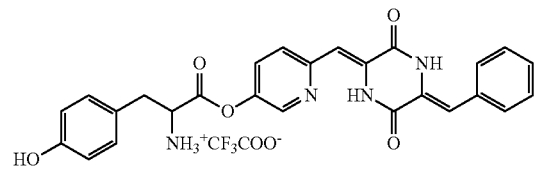

Compound 12 was prepared in a manner similar to those described in Examples 8 and 9.

mp 312-314° C.; $^1$H-NMR (500 MHz, CDCl$_3$), δ 2.54 (s, 1H) 3.18 (m, 2H), 4.79 (m, 1H), 5.23 (m, 2H) 6.76 (s, 1H), 7.10 (s, 1H), 7.04-7.52 (m, 11H), 8.24 (s, 1H), 8.28 (s, 1H), 12.43 (s, 1H).

Example 13

Synthesis of 6-((Z)—((Z)-5-benzylidene-3,6-dioxopiperazin-2-ylidene)methyl)pyridin-3-yl-2-(tert-butoxycarbonylamino)-3-(4-tert-butoxyphenyl)propanoate (Compound 13)

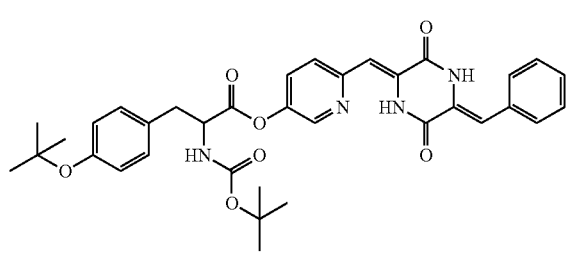 [SMILES: CC(C)(C)OC(=O)NC(Cc1ccc(OC(C)(C)C)cc1)C(=O)Oc1ccc(/C=c2\[nH]c(=O)/c(=C/c3ccccc3)[nH]c2=O)nc1]

Compound 13 was prepared in a manner similar to that described in Example 8. mp 210-212° C.; $^1$H-NMR (500 MHz, CDCl$_3$), δ 1.36 (s, 9H) 1.46 (s, 9H), 3.15 (m, 2H), 4.79 (m, 1H), 5.06 (d, J=7.2 Hz, 1H), 6.76 (s, 1H), 7.00 (s, 1H), 7.14-7.48 (m, 11H), 8.22 (s, 1H), 8.24 (s, 1H), 12.43 (s, 1H).

Example 14

Synthesis of (3Z,6Z)-6-benzylidene-3-((5-(pyridin-4-ylmethoxy)pyridin-2-yl)meth-ylene)-1-(pyridin-4-ylmethyl)piperazine-2,5-dione (Compound 14)

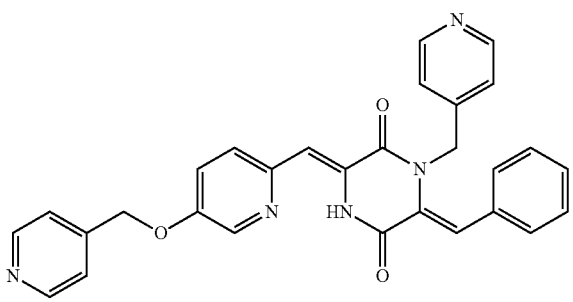 [SMILES: O=c1[nH]/c(=C\c2ccc(OCc3ccncc3)cn2)c(=O)n(Cc2ccncc2)/c1=C\c1ccccc1]

To a solution of Compound C (0.39 g) and 4-chloromethylpyridine HCl salt (0.416 g) in DMF (10 mL) were added K$_2$CO$_3$ (0.7 g) and KI (0.1 g) sequentially. The solution was stirred at 60~80° C. for 8 hr. After the completion of the reaction, DMF was removed by rotary evaporator and the residue was further partitioned by brine and CH$_2$Cl$_2$. The CH$_2$Cl$_2$ layer was collected and the solvent was removed by rotary evaporator. The residue was subjected to column chromatography eluated with EtOAc to obtained Compound 14 as a dark yellow solid (0.28 g, 45%): mp 284° C. decomp;

$^1$HNMR (400 MHz, DMSO): δ 5.347 (s, 2H), 5.564 (s, 2H), 6.620 (s, 2H), 7.165 (s, 2H), 7.353~8.61 (m, 16H).

Example 15

Synthesis of ((R)-2-{6-[3,6-Dioxo-5-[1-phenyl-meth-(Z)-ylidene]-piperazin-(2Z)-ylidenemethyl]-pyridin-3-yloxy}-1-phenyl-ethyl)-carbamic acid tert-butyl ester (Compound 15)

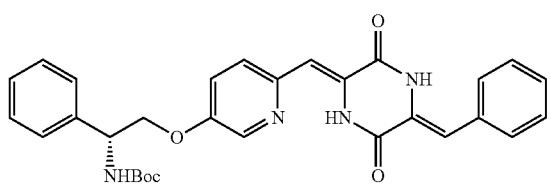 [SMILES: CC(C)(C)OC(=O)N[C@@H](COc1ccc(/C=c2\[nH]c(=O)/c(=C/c3ccccc3)[nH]c2=O)nc1)c1ccccc1]

Compound 15 was prepared in a manner similar to that described in Example 1.

mp=199~200° C.; NPTLC R$_f$=0.5 (2% MeOH in CHCl$_3$); IR (KBr): 3236, 3132, 3088, 3062, 3030, 2976, 2926, 1697, 1649, 1593, 1479, 1444, 1390, 1365, 1238, 1171, 1072, 945, 746 cm$^{-1}$; $^1$H-NMR (400 MHz, CDCl$_3$) δ1.47 (s, 9H), 4.35-4.38 (m, 2H), 5.13 (s, 1H), 5.25-5.27 (m, 1H), 6.74 (s, 1H), 7.09 (s, 1H), 7.25-7.50 (m, 13H), 8.22 (s, 1H), 8.36 (s, 1H), 12.51 (s, 1H); HRMS (EI) calcd for C$_{30}$H$_{30}$N$_4$O$_5$ 526.2216. found 526.2216.

Example 16

Synthesis of trifluoro-acetate(R)-2-{6-[3,6-dioxo-5-[1-phenyl-meth-(Z)-ylidene]-piperazin-(2Z)-ylidenemethyl]-pyridin-3-yloxy}-1-phenyl-ethyl-ammonium (Compound 16)

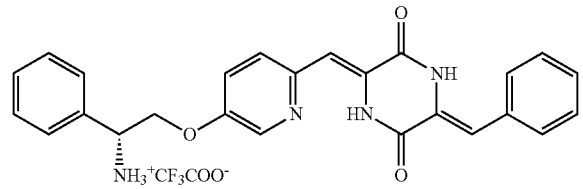

Compound 15 (102 mg, 0.19 mmole) was dissolved in 10 ml of dichloromethane and then 2.5 ml of trifluoroacetic acid (TFA) was added slowly at 0° C. The reaction mixture was stirred at 0° C. and monitored by TLC until disappearance of the starting material. TFA was removed by a rotary evaporator and the crude compound was recrystallized in acetonitrile to give Compound 16 as a yellow solid (yield: 93%). mp=168~169° C.; RPTLC R$_f$=0.63 (CHCl$_3$:MeOH:TEA=9:1:0.1); IR (KBr): 3469, 3386, 3169, 3057, 2926, 2885, 1682, 1641, 1493, 1446, 1416, 1387, 1352, 1267, 1201, 1134, 1038, 941 cm$^{-1}$; $^1$H-NMR (400 MHz, DMSO-d$_6$) δ 4.40-4.50 (m, 2H), 4.83 (dd, J=4.0 Hz, 8.0 Hz, 1H), 6.74 (s, 1H), 6.84 (s, 1H), 7.33-7.37 (m, 1H), 7.42-7.63 (m, 10H), 7.69-7.71 (m, 1H), 8.55-8.56 (m, 2H), 12.28 (s, 1H).

Example 17

Synthesis of 3-((5-(benzyloxy)pyridin-2-yl)methylene)-6-(3-(3-(dimethylamino)propoxy)benzylidene)piperazine-2,5-dione (Compound 17)

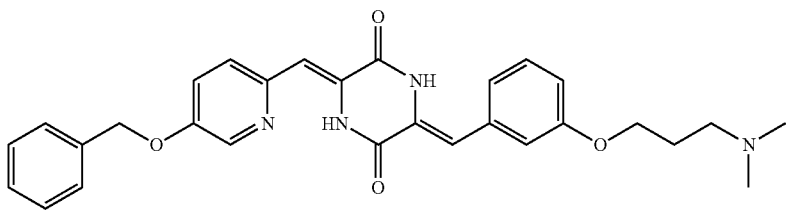 [SMILES: CN(C)CCCOc1cccc(/C=c2\[nH]c(=O)/c(=C/c3ccc(OCc4ccccc4)cn3)[nH]c2=O)c1]

Compound 17 was prepared in manner similar to that described in Example 1.

mp: 286° C. decomp. $^1$HNMR (400 MHz, DMSO) δ2.369 (m, 2H, N—CH$_2$—CH$_2$—CH$_2$), 2.779 (s, 6H, N—(CH$_3$)$_2$), 3.279 (t, 2H, N—CH$_2$), 4.112 (t, 2H, O—CH$_2$), 5.169 (s, 2H, Ph-CH$_2$), 6.877 (s, 1H, Ph-CH), 7.002 (s, 1H, 2-pyridine-CH), 7.3~8.423 (m, 12H, aromatic H) ppm.

Example 18

Synthesis of 6-benzylidene-3-((5-(2-hydroxyethoxy)pyridin-2-yl)methylene)-1-(2-hydroxyethyl)piperazine-2,5-dione (Compound 18)

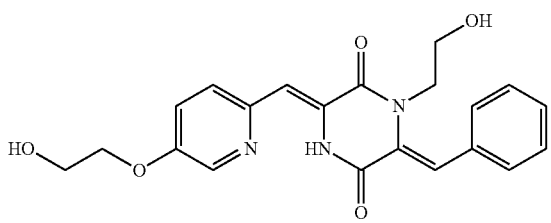 [SMILES: O=c1[nH]/c(=C\c2ccc(OCCO)cn2)c(=O)n(CCO)/c1=C\c1ccccc1]

Compound 18 was prepared in a manner similar to that described in Example 14.

mp: 326° C. decomp. $^1$HNMR (400 MHz, DMSO) δ 3.741 (t, 2H, N—CH$_2$—CH2OH), 4.126 (t, 2H, N—CH$_2$—CH$_2$OH), 4.405 (t, 2H, pyridine-2-yl-O—CH$_2$—CH$_2$OH), 5.303 (t, 2H, pyridine-2-yl-O—CH$_2$—CH$_2$OH), 6.529 (s, 1H, Ph-CH=C), 7.148 (s, 1H, pyridine-2-yl-CH=C), 7.318~8.463 (m, 8H, aromatic) ppm.

Examples 19 and 20

Synthesis of 1-acetyl-3-(quinolin-2-ylmethylene)piperazine-2,5-dione and compound 21, 3,6-bis(quinolin-2-ylmethylene)piperazine-2,5-dione (Compounds 19 and 20)

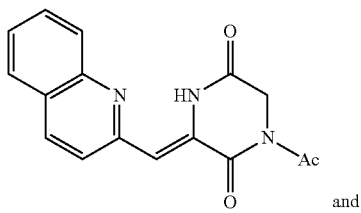

and

-continued

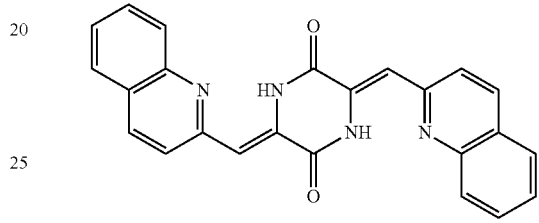

To a mixture of quinoline-2-carbaldehyde (4.72 g, 30 mmle), triethylamine (4.6 mL, 63.6 mmole), and tetrabutylammonium bromide (9.67 g, 30 mmole) in 50 mL of DMF was added 1,4-diacetyl-piperazine-2,5-dione (7.93 g, 40 mmole). The reaction was stir for 24 hr at room temperature and monitored by TLC. After reaction was complete, the reaction mixture was cooled in an ice-bath to allow precipitation. The solid was collected by filtration, recrystallized it in DMF, and rinsed by EtOAc to get compound 19 (0.23 g, yield 2%). After the filtrate was cooled, yellow needle crystal was obtained as compound 20 (6.28 g, yield 71%).

Compound 19: mp=262-263° C.; IR (KBr) 1681, 1643, 1555, 1505, 1453 cm$^{-1}$; EI-MS (70 eV), m/z=295.1, 210.1, 168.2, 140.2, 128.2; $^1$HNMR (400 MHz, DMSO) 2.54 (3H, s, COCH$_3$), 4.40 (2H, s, —N—CH$_2$—CO—N—), 7.01 (1H, s, —CH=C), 7.65 (1H, m, quinoline H-3), 7.83 (2H, m, quinoline H-6, H-7), 7.99 (2H, m, quinoline H-4, H-5), 8.46 (1H, d, J=8.4 Hz, quinoline H-8), 13.04 (1H, s, CONH).

Compound 20: mp=374-375° C.; IR (KBr) 1682, 1644, 1555, 1537, 1504, 1455 cm$^{-1}$; EI-MS (70 eV), m/z=392.2, 364.2, 236.1, 168.1, 140.1, 128.1; $^1$HNMR (400 MHz, TFA-D90%+DMSO-D$_6$10%) 7.11 (2H, sx2, (—CH=C)X2), 7.62 (2H, m, (quinoline H-3)X2), 7.85 (8H, m, (quinoline H-4, H-5, H-6, H-7)X2), 8.73 (2H, d, J=8.4 Hz, (quinoline H-8)X2)

Example 21

Synthesis of 3-(pyridin-3-ylmethylene)-6-(quinolin-2-ylmethylene)piperazine-2,5-dione (Compound 21)

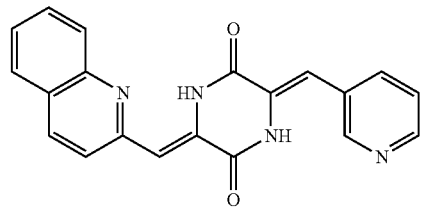 [SMILES: O=c1[nH]/c(=C\c2ccc3ccccc3n2)c(=O)[nH]/c1=C\c1cccnc1]

To a warm solution of 1-acetyl-3-(quinolin-2-ylmethylene)piperazine-2,5-dione (compound 20, 1.06 g, 3.59 mmole) and triethylamine (2 mL, 27.67 mmole) in 150 mL DMF was added pyridine-3-carbaldehyde (0.45 mL, 4.8 mmole). The reaction was stirred at 100° C. for 24 hr and monitored by TLC. After the reaction was complete, it was cooled in an ice-bath to allow precipitation. Solid was collected by filtration and washed by EtOAc, and then recrystallized in DMF to get 0.73 g powdery compound 21 (yield: 59%).

mp=305-306° C.; IR (KBr) 2921, 1681, 1643, 1555, 1428 cm$^{-1}$; EI-MS (70 eV), m/z=342.2, 186.1, 182.1, 168.1, 128.1; $^1$HNMR (400 MHz, DMSO) δ6.87 (2H, sx2, (—CH═C)X2), δ7.44 (1H, m, pyridine H-5), δ 7.64 (1H, m, quinoline H-3), 7.78 (1H, m, quinoline H-6), 7.85 (1H, m, quinoline H-7), 7.96 (1H, d, J=8.0 Hz, pyridine H-4), 8.00 (2H, m, quinoline H-4, H-5), 8.44 (1H, d, J=8.4 Hz, quinoline H-8), 8.50 (1H, s, pyridine H-6), 8.72 (1H, s, pyridine H-2), 10.84 (1H, s, CONH), 13.21 (1H, s, CONH).

Example 22

Synthesis of 3-(4-fluorobenzylidene)-6-(quinolin-2-ylmethylene)piperazine-2,5-dione (Compound 22)

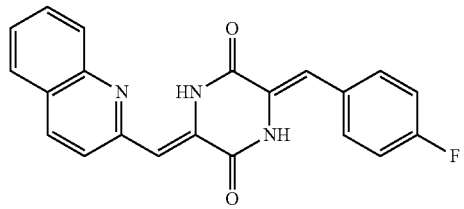 [SMILES: O=c1[nH]/c(=C\c2ccc3ccccc3n2)c(=O)[nH]/c1=C\c1ccc(F)cc1]

Compound 22 was prepared in a similar manner to that described in Example 20. mp=319-320° C.; IR (KBr) 1681, 1644, 1555, 1537, 1505, 1455 cm$^{-1}$; EI-MS (70 eV), m/z=359.1, 331.2, 182.1, 168.1, 136.1, 128.1; $^1$HNMR (400 MHz, DMSO) δ 6.86 (1H, s, —CH═C), 6.88 (1H, s, —CH═C), 7.26 (2H, m, phenyl H-3, H-5), 7.62 (2H, m, phenyl H-2, H-6), 7.65 (1H, m, quinoline H-3), 7.77 (1H, m, quinoline H-6), 7.85 (1H, m, quinoline H-7), 8.00 (2H, m, quinoline H-4, H-5), 8.44 (1H, d, J=8.4 Hz, quinoline H-8), 10.53 (1H, s, CONH), 13.17 (1H, s, CONH).

Example 23

Synthesis of 3-(4-chlorobenzylidene)-6-(quinolin-2-ylmethylene)piperazine-2,5-dione (Compound 23)

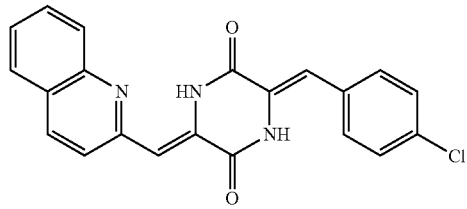 [SMILES: O=c1[nH]/c(=C\c2ccc3ccccc3n2)c(=O)[nH]/c1=C\c1ccc(Cl)cc1]

Compound 23 was prepared in a manner similar to that described in Example 22.

mp=348-349° C.; IR (KBr) 1682, 1643, 1555, 1538, 1504, 1455 cm$^{-1}$; EI-MS (70 eV), m/z=375.1, 347.1, 182.1, 168.1, 152.0, 142.1, 128.1; $^1$HNMR (400 MHz, DMSO) δ 6.86 (2H, s, 2 (—CH═C)), 7.47 (2H, d, J=8.4 Hz, phenyl H-3, H-5), 7.58 (2H, d, J=8.4 Hz, phenyl H-2, H-6), 7.64 (1H, m, quinoline H-3), 7.76 (1H, m, quinoline H-6), 7.84 (1H, m, quinoline H-7), 7.99 (2H, m, quinoline H-4, H-5), 8.43 (1H, d, J=8.4 Hz, quinoline H-8), 10.54 (1H, s, CONH), 13.18 (1H, s, CONH).

Example 24

Synthesis of 3-(quinolin-2-ylmethylene)-6-(thiophen-2-ylmethylene)piperazine-2,5-dione (Compound 24)

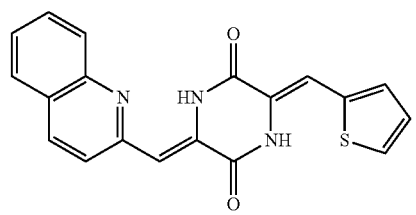 [SMILES: O=c1[nH]/c(=C\c2cccs2)c(=O)[nH]/c1=C\c1ccc2ccccc2n1]

Compound 24 was prepared in manner similar to that described in Example 22.
mp=288-289° C.; IR (KBr) 2920, 1690, 1643, 1555, 1504, 1454 cm$^{-1}$; EI-MS (70 eV), m/z=347.1, 319.1, 182.1, 168.1, 124.1; $^1$HNMR (400 MHz, DMSO) δ 6.88 (1H, s, 7.05 (1H, s, —CH═C), 7.21 (1H, m, thiophene H-4), 7.64 (2H, m, quinoline H-3, thiophene H-5), 7.78 (2H, m, quinoline H-6, thiophene H-3), 7.84 (1H, m, quinoline H-7), 7.99 (2H, m, H$_4$, quinoline H-5), 8.44 (1H, d, J=8.4 Hz, quinoline H-8), 9.95 (1H, s, CONH), 13.18 (1H, s, CONH).

Examples 25 and 26

Synthesis of 1-acetyl-3-(quinolin-4-ylmethylene)piperazine-2,5-dione and compound 27, 3,6-bis(quinolin-4-ylmethylene)piperazine-2,5-dione (Compounds 26 and 27)

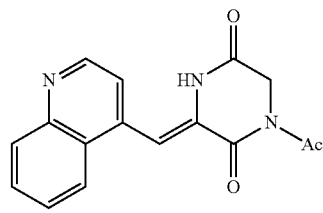

and

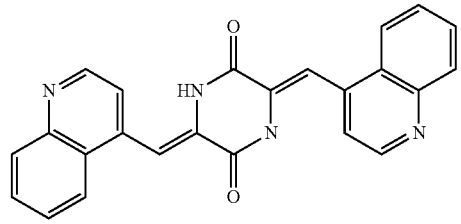

Compound 25 and compound 25 were synthesized in a manner similar to that described in Examples 19 and compound 20.

Compound 25: mp=239-24° C.; EI-MS (70 eV), m/z=295.0, 253.1, 224.1, 196.1, 168.2, 140.1; $^1$HNMR (200 MHz, DMSO) δ 2.52 (3H, s, COCH$_3$), 4.34 (2H, s, —N—CH$_2$—CO—N—), 7.29 (1H, s, —CH=C), 7.50 (1H, d, J=4.4 Hz, quinoline H-3), 7.60 (1H, m, quinoline H-6), 7.76 (1H, m, quinoline H-7), 7.95 (1H, d, J=8.6 Hz, quinoline H-5) 8.03 (1H, d, J=8.4 Hz, quinoline H-8), 8.88 (1H, d, J=4.4 Hz, H$_2$), 10.36 (1H, s, CONH).

Compound 26: mp=374-375° C.; IR (KBr) 3229, 1685, 1632, 1586, 1505, 1410 cm$^{-1}$; EI-MS (70 eV), m/z=392.0, 264.1, 197.1, 168.1, 140.1; $^1$HNMR (400 MHz, DMSO) δ 6.86 (2H, sx2, (—CH=C)X2), 7.57 (2H, d, J=4.4 Hz, (quinoline H-3)X2), 7.65 (2H, m, (quinoline H-6)X2), 7.78 (2H, m, (quinoline H-7)X2), 7.98 (2H, d, J=8.4 Hz, (quinoline H-5) X2) 8.07 (2H, d, J=8.4 Hz, (quinoline H-8)X2), 8.92 (2H, d, J=4.4 Hz, (quinoline H-2)X2), 10.62 (2H, s, (CONH)X2).

Example 27

Synthesis of 1-acetyl-3-(quinolin-3-ylmethylene)piperazine-2,5-dione (Compound 27)

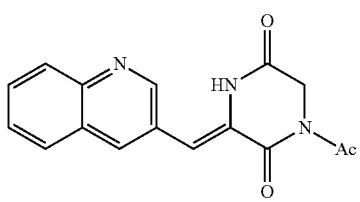 [SMILES: CC(=O)N1CC(=O)N/C(=C\c2cnc3ccccc3c2)C1=O]

To a mixture of quinoline-3-carbaldehyde (0.472 g, 3 mmole) and triethylamine (1.66 mL, 23 mmole) in 10 mL DMF was added 1,4-diacetyl-piperazine-2,5-dione (0.654 g, 3.3 mmole). The reaction was stirred for 24 hr at room temperature. After the reaction was complete, it was cooled by an ice-bath to allow precipitation. A yellow solid was collected, washed by EtOAc, and recrystallized in 5 mL hot DMF to give compound 27 as a yellow needle crystal (0.602 g, yield: 68%). mp=261-262° C.; IR (KBr) 1693, 1631, 1572, 1496, 1408 cm$^{-1}$; EI-MS (70 eV), m/z=295.0, 253.1, 224.1, 196.1, 168.2, 140.1; $^1$HNMR (400 MHz, DMSO) δ 2.52 (3H, s, COCH$_3$), 4.40 (2H, s, —N—CH$_2$—CO—N—), 7.12 (1H, s, —CH=C), 7.63 (1H, m, quinoline H-6), 7.77 (1H, m, quinoline H-7), 8.01 (2H, m, quinoline H-5, H-8), 8.33 (1H, s, quinoline H-4), 9.01 (1H, s, quinoline H-2), 10.75 (1H, s, CONH)

Example 28

Synthesis of (Z)-3-benzyl-6-((5-hydroxypyridin-2-yl)methylene)piperazine-2,5-dione (Compound 28)

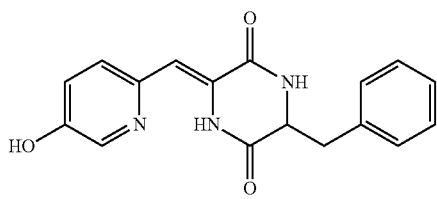 [SMILES: O=C1NC(Cc2ccccc2)C(=O)N/C1=C\c1ccc(O)cn1]

Compound C in Example 1 was added to a solution of NH$_4$Cl (10 eq, 0.3 M) in DMF with zinc powder (10 eq). The reaction was stirred in an ice bath for 2 hr. After the reaction was complete, the reaction mixture was filtered. The filtrate was collected and water (2× to DMF) was added. The solid precipitate was collected. The collected solids were combined, washed with water, and dried to give a white powder (yield: 78%). mp. 251-252° C. $^1$H-NMR (400 MHz, DMSO-d6) δ 3.04 (dd, J=4.0, 11.2 Hz, 1H), 3.13 (dd, J=3.6, 11.2 Hz, 1H), 4.32 (dd, J=4.0, 6.0 Hz, 1H), 6.41 (s, 1H), 7.01 (d, J=1.2 Hz, 2H, ArH), 7.24-7.36 (m, 5H, ArH), 7.92 (s, 1H, ArH), 8.26 (d, J=1.6 Hz, 1H, NH), 9.60 (s, 1H, OH), 9.71 (s, 1H, NH)

Example 29

Synthesis of (Z)-6-((5-benzyl-3,6-dioxopiperazin-2-ylidene)methyl)pyridin-3-yl-2-((tert-butoxycarbonyl)amino)-2-phenylacetate (Compound 29)

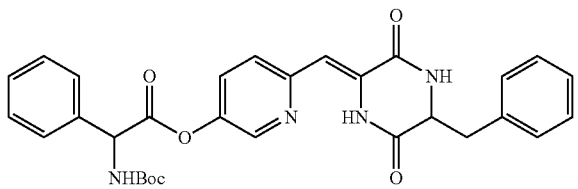 [SMILES: CC(C)(C)OC(=O)NC(C(=O)Oc1ccc(/C=C2\NC(=O)C(Cc3ccccc3)NC2=O)nc1)c1ccccc1]

Compound 29 was synthesized in a manner similar to that described in Example 28 excempt that compound 16 as the starting material. mp: 171.5~173.5° C. $^1$H-NMR (400 MHz, DMSO-d6) δ 1.38 (s, 9H, Boc), 3.20 (dd, J=4.4, 11.6 Hz, 1H), 3.26 (dd, J=4.0, 11.6 Hz, 1H), 4.43-4.44 (m, 1H), 5.43 (d, J=6.0 Hz, 1H), 6.48 (s, 1H), 7.28-7.46 (m, 13H, ArH), 8.10 (s, 1H, NH), 8.35 (s, 1H, NH), 9.78 (s, 1H, NH).

Example 30

Kinome Inhibition Assay

Kinome inhibition studies were conducted following the procedures described in literature. See, e.g., Ozawa T, et al., *Anal. Chem.* 1998, 70:2345-2352; Buchdunger D, et al., *Cancer Res.* 1996, 56:100-104; and Farley K, et al., *Anal. Biochem.* 1992, 203:151-157. In general, each purified kinase was incubated with its substrate in buffer (MOPS buffer or HEPES buffer) containing an essential metal co-enzyme or cofactor, antioxidant, and ATP (gamma-P$^{32}$ radio-labeled ATP or cold ATP). Compound 2 was co-incubated with the kinase solution thus obtained for 0.5-1 hr at 37° C. The reaction was stopped by boiling the reaction solution with an extra SDS solution. The phosphorylation level of the substrate was monitored ether by quantification of the radio-labeled substrate or by quantification of phosphor-substrate specific antibodies. In each study, a reference standard was run as an integral part to ensure the validity of the experimental results obtained. The table below includes the IC$_{50}$ values obtained from this experiment.

|  | Enzyme | Species | IC$_{50}$ | Single dose inhibition |
|---|---|---|---|---|
| Tyrosine kinase inhibitor activity | Insulin Receptor | Human | 1.83 µM | 70% @ 3 µM |
|  | ABL1 | Mouse | 3.17 µM | 90% @ 10 µM |
|  | RET | Human | 4.89 µM | 73% @ 10 µM |
|  | ERBB2 (HER2) | Human | 5.56 µM | 69% @ 10 µM |
|  | FER (TYK3) | Human | 7.23 µM | 55% @ 10 µM |

-continued

|  | Enzyme | Species | $IC_{50}$ | Single dose inhibition |
|---|---|---|---|---|
|  | MET (HGFR) | Human | 12.3 µM | 79% @ 30 µM |
|  | NTRK1 (TRKA) | Human | 17.4 µM | 66% @ 30 µM |
| Serine/ | SGK1 | Human | 2.92 µM | 83% @ 10 µM |
| Threonine | SGK2 | Human | 3.55 µM | 78% @ 10 µM |
| kinase | AKT1 (PRKBA) | Human | 3.93 µM | 93% @ 10 µM |
| inhibitor | MAPK8 (JNK1) | Human | 4.79 µM | 74% @ 10 µM |
| activity | LMK1 | Human | 5.8 µM | 68% @ 10 µM |
|  | CAMK2D (KCC2D) | Human | 7.39 µM | 70% @ 10 µM |
|  | RP56KA5 (MSK1) | Human | 7.88 µM | 53% @ 10 µM |
|  | PDK1 | Human | 8.18 µM | 59% @ 10 µM |
|  | CDC42BPB | Human | 8.18 µM | 52% @ 10 µM |
|  | PIM1 | Human | 9.52 µM | 98% @ 30 µM |
|  | GSK3B | Human | 10.9 µM | 69% @ 30 µM |
|  | AURKA (Aurora-A) | Human | 13.7 µM | 73% @ 30 µM |
| Serine/ Arginine-rich kinase inhibitor activity | SRPK1 | Human | 10.6 µM | 61% @ 10 µM |

Example 31

Broad-Spectrum Anticancer Activities of Compound 2, 8 and 9 Against 60 Human Cancer Cell Lines (NCI-60)

Broad-spectrum anticancer activities were conducted by NCI/NIH following standard protocols.

Human tumor cell lines were grown in RPMI 1640 medium containing 5% fetal bovine serum and 2 mM L-glutamine. For a typical screening experiment, cells were inoculated into 96-well microtiter plates in 100 µL at the plating densities ranging from 5,000 to 40,000 cells/well depending on the doubling time of individual cell lines. After cell inoculation, the microtiter plates were incubated at 37° C., 5% CO2, 95% air and 100% relative humidity for 24 h prior to addition of experimental drugs.

After 24 h, two plates of each cell line were fixed in situ with TCA, to represent a measurement of the cell population for each cell line at the time of drug addition (Tz). Experimental drugs were solubilized in dimethyl sulfoxide at 400-fold the desired final maximum test concentration and stored frozen prior to use. At the time of drug addition, an aliquot of frozen concentrate was thawed and diluted to twice the desired final maximum test concentration with complete medium containing 50 µg/ml gentamicin. Additional four, 10-fold or ½ log serial dilutions were made to provide a total of five drug concentrations plus control. Aliquots of 100 µl of these different drug dilutions were added to the appropriate microtiter wells already containing 100 µl of medium, resulting in the required final drug concentrations.

Following drug addition, the plates were incubated for an additional 48 h at 37° C., 5% CO2, 95% air, and 10% relative humidity. For adherent cells, the assay was terminated by the addition of cold TCA. Cells were fixed in situ by the gentle addition of 50 µl of cold 50% (w/v) TCA (final concentration, 10% TCA) and incubated for 60 minutes at 4° C. The supernatant was discarded, and the plates were washed five times with tap water and air dried. Sulforhodamine B (SRB) solution (100 µl) at 0.4% (w/v) in 1% acetic acid was added to each well, and plates were incubated for 10 minutes at room temperature. After staining, unbound dye was removed by washing five times with 1% acetic acid and the plates were air dried. Bound stain was subsequently solubilized with 10 mM trizma base, and the absorbance was read on an automated plate reader at a wavelength of 515 nm. For suspension cells, the methodology was the same except that the assay was terminated by fixing settled cells at the bottom of the wells by gently adding 50 µl of 80% TCA (final concentration, 16% TCA). Using the seven absorbance measurements [time zero, (Tz), control growth, (C), and test growth in the presence of drug at the five concentration levels (Ti)], the percentage growth was calculated at each of the drug concentrations levels. Percentage growth inhibition was calculated as:

$[(Ti-Tz)/(C-Tz)] \times 100$ for concentrations for which $Ti >/= Tz$ $[(Ti-Tz)/Tz] \times 100$ for concentrations for which $Ti < Tz$.

Three dose response parameters were calculated for each experimental agent. Growth inhibition of 50% (GI50) is calculated from $[(Ti-Tz)/(C-Tz)] \times 100=50$, which is the drug concentration resulting in a 50% reduction in the net protein increase (as measured by SRB staining) in control cells during the drug incubation. The drug concentration resulting in total growth inhibition (TGI) is calculated from Ti=Tz. The LC50 (concentration of drug resulting in a 50% reduction in the measured protein at the end of the drug treatment as compared to that at the beginning) indicating a net loss of cells following treatment is calculated from $[(Ti-Tz)/Tz] \times 100=-50$. Values were calculated for each of these three parameters if the level of activity is reached; however, if the effect is not reached or is exceeded, the value for that parameter is expressed as greater or less than the maximum or minimum concentration tested.

The $pIC_{50}$ values of Compound 2 were calculated by the following equation:

$pIC_{50} = -\log(IC_{50})$, where $IC_{50}$ represents the compound concentration required for 50% inhibition of certain cancer cells.

The mean $pIC_{50}$ value of Compound 2 (against leukemia, NSCLC, colon cancer, central nervous system cancer, melanoma, ovarian cancer, renal cancer, prostate cancer, and breast cancer) was 7.28. This indicates that Compound 2 is a more potent anticancer agent than Gleevec ($pIC_{50}$ 4.82*), Irressa ($pIC_{50}$ 5.49*), Tarceva ($pIC_{50}$ 5.26*), Mexavar ($pIC_{50}$ 5.73*), Sutent ($pIC_{50}$ 5.71*), Alimta ($pIC_{50}$ 4.97*), Gemcitabine ($pIC_{50}$ 6.82*), 5-FU ($pIC_{50}$ 4.76*), MTX ($pIC_{50}$ 6.95*), irinotecan ($pIC_{50}$ 4.85*), cisplatin ($pIC_{50}$ 45.60*), and eloxatin ($pIC_{50}$ 5.65*). Its anticancer activity is comparable to those of taxol ($pIC_{50}$ 7.84*) and docetxel ($pIC_{50}$ 7.66*). The asterisk denotes data obtained from the NCI/DTP database.

The anticancer dose in human was calculated according to the US FDA Human Equivalent Dose Calculation method. See Guidance of Industry-Estimating the Maximum Safe Starting Dose in Initial Clinic Trial for Therapeutics in Adult Healthy Volunteers published by the US FDA Center for Drug Evaluation and Research in 2005. The suggested dose in human is 24.3 mg/day, which is much lower than most market anticancer drugs.

Example 32

In Vitro Growth Inhibition on PC-3 Human Prostate Cancer Cell Line

The sulforhodamine B assay for anticancer screening was conducted on PC-3 cells. Cells were seeded in 96-well plates in medium with 5% FBS. After 24 h, cells were fixed with 10% trichloroacetic acid (TCA) to represent cell population at the time of compound addition (T0). After additional incubation of DMSO or compound for 48 h, cells were fixed with 10% TCA and SRB at 0.4% (w/v) in 1% acetic acid was added to stain cells. Unbound SRB was washed out by 1% acetic acid and SRB bound cells were solubilized with 10 mM Trizma base. The absorbance was read at a wavelength of 515 nm. Using the following absorbance measurements, such as time zero (T0), control growth (C), and cell growth in the presence of the compound (Tx), the percentage growth was calculated at each of the compound concentrations levels. Percentage growth inhibition was calculated as: 100−[(Tx−T0)/(C−T0)]×100. Growth inhibition of 50% (IC50) is determined at the compound concentration which results in 50% reduction of total protein increase in control cells during the compound incubation.

Compounds 1-20 exhibited potent antitumor activities against PC-3 human prostate cancer line. Their $IC_{50}$ values are between 0.01 μM and less than 10 μM.

Example 33

Inhibition of Cancer Cells by Compound 2

Male SCID mice, 12 weeks old with the body weight ranging from 22.4 g to 31.6 g, were fed ad libitum water (reverse osmosis, 1 ppm Cl) and PicoLab Rodent Diet 20 (Modified and Irradiated Lab Diet® consisting of 20.0% crude protein, 9.9% crude fat, and 4.7% crude fiber). The mice were housed on a 12-hour light cycle at 21-23° C. and 60-85% humidity (National Taiwan University Laboratory Animal Center, NTUMC). Nude-athymic mice were maintained in accordance with the Institutional Animal Care and Use Committee procedures and guidelines.

Human HL-60 promyelocytic leukemia cells were maintained in RPMI 1640 medium containing 100 units/mL penicillin G sodium, 100 μg/mL streptomycin sulfate, 0.25 μg/mL amphotericin B, and 25 μg/mL gentamicin. The medium was supplemented with 10% heat-inactivated fetal bovine serum and 2 mM glutamine. The cells were cultured in tissue culture flasks in a humidified incubator at 37° C., in an atmosphere of 5% CO2 and 95% air.

The human HL-60 promyelocytic leukemia cells used for implantation were harvested during log phase growth and resuspended in phosphate-buffered saline at $8.0 \times 10^7$ cells/mL. Each mouse was injected s.c. in the right flank with 1.6×107 cells (0.2 mL cell suspension). Tumors were monitored twice weekly and then daily as their volumes approached 100 mm³. On D1 of the study, the animals were sorted into treatment groups with tumor sizes of 106.6-1171.5 mm3 and group mean tumor sizes of ~444.4 mm³. Tumor size, in mm3, was calculated as: Tumor Volume=w2×l, where w=width and l=length in mm of the tumor. Tumor weight can be estimated with the assumption that 1 mg is equivalent to 1 mm3 of tumor volume.

Compound 2 was administered orally (p.o.) in a 0.5% carboxyl methyl cellulose solution. The agent was given dose at 5 mg/kg once every day (qd) and every other day (q2d) to endpoint. Treatments began on Day 1 (D1) in groups of male SCID mice (n=6) bearing established (~444.4 mm3) subcutaneous tumors. The study duration was 29 days. Treatment results were presented as percent tumor growth delay (% TGD), which is the percent increase in the median time to endpoint (TTE) for drug-treated versus control mice. Logrank tests determine significance of the differences between TTE values for drug-treated and control mice, at P≤0.05. The median TTE for the control group was 11.0 days.

Compound 2 at 5 mg/kg once a day produced a median TTE of 14.2 days, corresponding to a 3.2-day T−C and a % TGD of 29. A maximum BW loss of 1.9% was observed on day 11. Two treatment related deaths occurred and thus not statistically evaluable. At every other day schedule, PE092002 produced a median TTE of 24.2 days, corresponding to a 13.2-day T−C and a % TGD of 120. A maximum BW loss of 4.2% was observed on day 8. In sum, Compound 2 at 5 mg/kg (q2d to end) demonstrated potent antitumor activity against human HL-60 promyelocytic leukemia xenograft in mice.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A compound of the following formula:

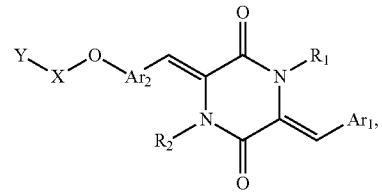

wherein
each of $R_1$ and $R_2$ is H or $C_{1-5}$ alkyl;
each of $Ar_1$ and $Ar_2$, independently, is aryl or heteroaryl;
X is methylene, C(O), or C(O)—$C_{1-3}$ alkylene; and
Y is heterocycloalkyl or heteroaryl.

2. The compound of claim 1, wherein X is $CH_2$.

3. The compound of claim 2, wherein $Ar_1$ is phenyl and $Ar_2$ is pyridinyl.

4. The compound of claim 3, wherein Y is pyridinyl.

5. The compound of claim 4, wherein Y is pyridin-4-yl.

6. The compound of claim 1, wherein $Ar_1$ is phenyl and $Ar_2$ is pyridinyl.

7. The compound of claim 1, wherein Y is pyridinyl.

8. The compound of claim 1, wherein the compound is selected from the group consisting of:

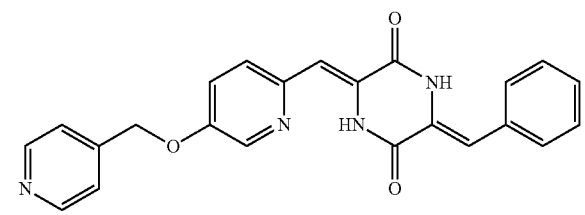

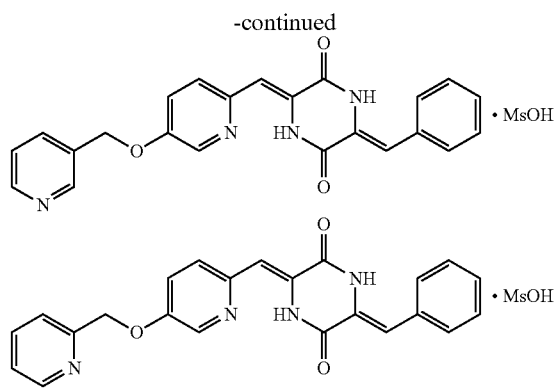

· MsOH

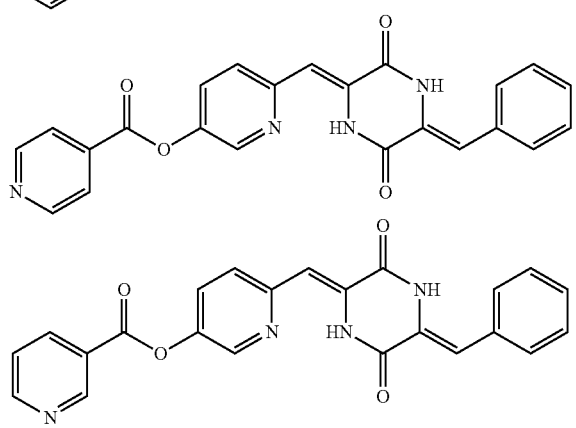

· MsOH

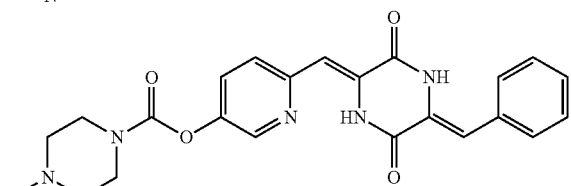

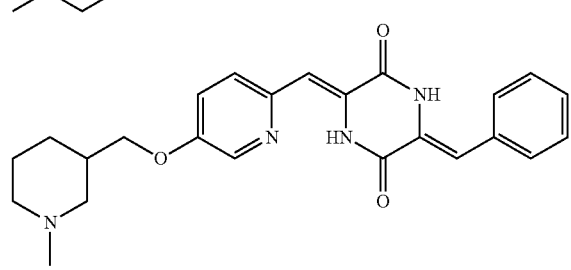

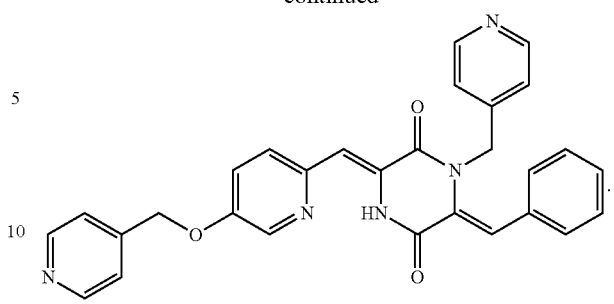

9. The compound of claim 1, wherein X is methylene substituted with amino or alkylcarbonylamino, C(O), or C(O)—$C_{1-3}$ alkylene substituted with amino or alkylcarbonylamino.

10. A method of treating cancer comprising administering to a subject in need thereof an effective amount of a compound of claim 1, wherein the cancer is bladder cancer, colon cancer, breast cancer, prostate cancer, renal cancer, hepatocellular cancer, lung cancer, ovarian cancer, cervical cancer, melanoma, brain tumors, acute myeloid leukemia, chronic myelogenous leukemia, acute lymphoblastic leukemia, chronic lymphocytic leukemia, Hodgkin's disease, non-Hodgkin's lymphoma, B-cell lymphoma, T-cell lymphoma, or multiple myeloma.

11. The compound of claim 1, wherein the compound is a methanesulfonate salt, a tosylate salt, or a napsylate salt of the following compound:

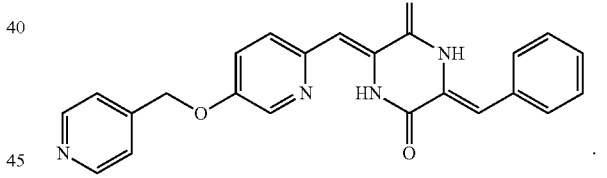

* * * * *